United States Patent [19]

Mori et al.

[11] Patent Number: 5,053,398

[45] Date of Patent: Oct. 1, 1991

[54] SULFATED HOMOPOLYSACCHARIDES AS ANTI-AIDS VIRUS AGENTS

[75] Inventors: Shigero Mori, Tokyo; Isamu Sugawara, Niiza; Wataru Ito, Kobe, all of Japan

[73] Assignee: Taito Co., Ltd., Tokyo, Japan

[21] Appl. No.: 349,634

[22] Filed: May 10, 1989

[30] Foreign Application Priority Data

May 13, 1988 [JP] Japan .................................. 63-116499

[51] Int. Cl.$^5$ ..................... A61K 31/715; C08B 37/00
[52] U.S. Cl. ........................................ 514/54; 536/122
[58] Field of Search ............................ 514/54; 536/122

[56] References Cited

U.S. PATENT DOCUMENTS

| | | | |
|---|---|---|---|
| 4,590,181 | 5/1986 | McCarthy | 514/54 |
| 4,783,446 | 11/1988 | Neushul | 514/54 |
| 4,840,941 | 6/1989 | Ueno et al. | 514/59 |
| 4,948,881 | 8/1990 | Naggi et al. | 536/20 |

FOREIGN PATENT DOCUMENTS 0293826 12/1988 European Pat. Off. .

OTHER PUBLICATIONS

Ehresmann et al., *Marine algae in Pharmaceutical Science*, Eds. H. A. Hoppe, T. Levring, Y. Tanaka, pp. 293-302 (1979), Walter de Gruyter, NY.
Ito et al., Eur. J. Clin. Microbiol. Infect. Dis., 8:171-173 (1989).
Sugawara et al., Experientia 45:996-998 (1989).
Ito et al., Antiviral Research, 7:361-367 (Jun. 1987).
Yoshida et al., Biochemical Pharmacology, 37(15):2887-2891 (Aug. 1988).
Bagasra et al., Journal of Infectious Diseases, 158(5):1084-1087 (Nov. 1988).
Agric. Biol. Chem., vol. 45, No. 2, 1981, pp. 525-526, Y. Iwamuro et al., "Structural Analysis of an Extracellular Polysaccharide of Porodisculus Pendulus".
Jpn. J. Exp. Med., vol. 58, No. 3, Jun. 1988, pp. 145-151, K. Mizumoto et al., "Sulfated Homopolysaccharides with Immunomodulating Activities are More Potent Anti-HTLV-III Agents than Sulfated Heteropolysaccharides".
Gann, vol. 60, Apr. 1969, pp. 137-144, N. Komatsu et al., "Host-mediated Antitumor Action of Schizophyllan, a Glucan Produced by Schizophyllum Commune".
Jpn. J. Cancer Res. (Gann), vol. 78, Nov. 1987, pp. 1164-1168, H. Nakashima et al., "Sulfation of Polysaccharides Generates Potent and Selective Inhibitors of Human Immunodeficiency Virus Infection and Replication in Vitro".
Agric. Biol. Chem., vol. 50, No. 6, 1986, p. 1635, T. Kojima et al., "Biological Activity of Sulfated Schizophyllan".
Antimicrobial Agents and Chemotherapy, vol. 31, No. 10, Oct. 1987, pp. 1524-1528, American Society for Microbiology, US, H. Nakashima et al., "Purification and Characterization of an Avian Myeloblastosis and Human Immunodeficiency Virus Reverse Transcriptase Inhibitor, Sulfated Polysaccharides extracted from Sea Algae".

*Primary Examiner*—Ronald W. Griffin
*Assistant Examiner*—Nancy S. Carson
*Attorney, Agent, or Firm*—Oblon, Spivak, McClelland, Maier & Neustadt

[57] ABSTRACT

An anti-AIDS virus agent comprising a sulfate of a polysaccharide having repeating units of the formula:

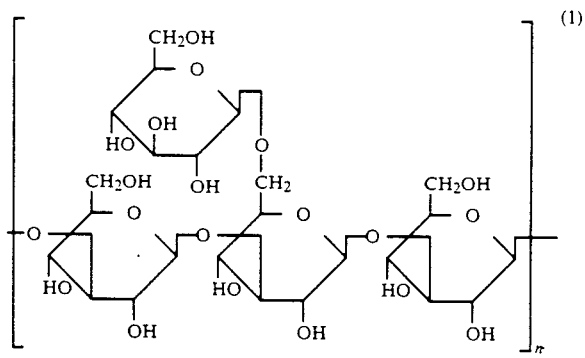

and having a molecular weight of at most 1,000,000 ($n \leq 1544$).

6 Claims, 2 Drawing Sheets

SULFATED HOMOPOLYSACCHARIDES AS ANTI-AIDS VIRUS AGENTS

The present invention relates to an anti-AIDS virus agent. More particularly, it relates to an anti-AIDS virus agent comprising a sulfate of a polysaccharide as an active ingredient.

AIDS (acquired immunodeficiency syndrome) is an infectious virus disease caused by HIV (human immunodeficiency virus) as the infectious virus. If infected with AIDS virus, helper T cells are mainly destroyed. Further, abnormality appears over the entire T cells or abnormality of B cells results, thus leading to immunological deficiency. As a result, opportunistic infection, malignant tumors such as Kaposi sarcoma or cerebral lymphoma, central nerve system and organ disorders will be brought about, and it is a dangerous disease which eventually leads to death.

There has been no drug which is capable of completely curing AIDS. However, substances such as azidothymidine (AZT), dideoxycytidine, dideoxyadenosine, suramin, ribavirin, HPA-23 and interferon, are known to exibit anti-AIDS effects. Among them, AZT has an activity to inhibit the reverse transcriptase of AIDS virus, and its use has been approved in U.S.A., since its usefulness to AIDS patients has been proved.

However, nucleoside-related substances including AZT have side effects and tend to lead to bone marrow disorders, macrocytic anemia, gastrointestinal disorders or lesions. No practical usefulness has been confirmed with suramin, ribavirin and HPA-23.

Recently, it has been found that polysaccharide SAE derived from Floridephyceae has an activity to inhibit the reverse transcriptase of AIDS virus. Further, polysaccharide sulfates derived from natural substances such as λ, k or ι-carrageenan, heparin or chondroitin sulfate, have similar physiological activities. On the other hand, studies are being made on the anti-AIDS virus activities of sulfates of various polysaccharides, and it has been found that dextran sulfate, xyloflanan sulfate and riboflanan sulfate, which are sulfates of polysaccharides having no anti-AIDS virus activities, such as dextran, xylofulanan and riboflanan, have anti-AIDS virus activities. A method of imparting anti-AIDS virus activities by sulfation to a substance having no such activities, is now being used as a technique for developing an anti-AIDS virus agent.

The following problems may be mentioned in the development of such polysaccharide sulfates as anti-AIDS virus agents:

(1) It is usually difficult to purify a polysaccharide, and a high level of technique is required for removing concomitant saccharides, proteins or pyrogeneous substances.

(2) The anti-AIDS virus activities vary depending upon the structure and the molecular weight of the polysaccharide and on the content of sulfate groups.

(3) When administered into a living body, it is likely to be decomposed by an enzyme in the body.

It is desired to solve these problems.

As a result of extensive researches on the physiological activities of polysaccharide sulfate, the present inventors have found that the intensity of so-called mitogenic activities which bring about non-specific blastogenesis varies depending upon the structure of the polysaccharide sulfate.

Namely, when mitogenic activities are compared as between a sulfate of a heteropolysaccharide composed of different types of monosaccharides and a sulfate of a homopolysaccharide composed of the same and one monosaccharide, the latter homopolysaccharide sulfate exhibits stronger mitogenic activities than the former heteropolysaccharide sulfate. As a result of a further study on the anti-AIDS virus activities, it has been found that the homopolysaccharide sulfate has stronger anti-AIDS virus activities than the heteropolysaccharide sulfate (The Japanese Journal of Experimental Medicine, Vol. 58, No. 3, pp. 147-153 (1988)).

On the basis of these discoveries, the present inventors have sulfated some homopolysaccharides and compared their anti-AIDS virus activites, whereby it has been found that dextran sulfate has stronger activities than the sulfates of e.g. mannan, pullulan and alginic acid. The present inventors have conducted further experiments on the anti-AIDS virus activities of other homopolysaccharide sulfates, and found that sulfates of polysaccharides consisting of the repeating unit represented by the formula (1) exhibit even stronger anti-AIDS virus activities than the dextran sulfate. They have further conducted tests on the effects of the molecular weight and the sulfate content of sulfates of the polysaccharides of the repeating unit of (1) over the anti-AIDS virus activities and have finally accomplished the present invention.

The present invention provides an anti-AIDS virus agent comprising a sulfate of a polysaccharide having repeating units of the formula:

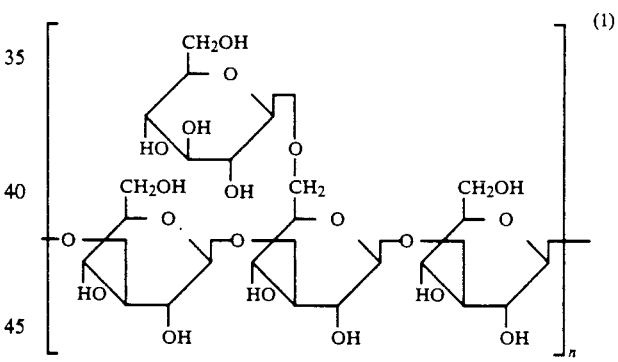

and having a molecular weight of at most 1,000,000 (n≦1544).

The present invention also provides use of a sulfate of a polysaccharide having repeating units of the formula (1) and having a molecular weight of at most 1,000,000 (n≦1544) for the manufacture of an anti-AIDS virus agent.

Figure 1:
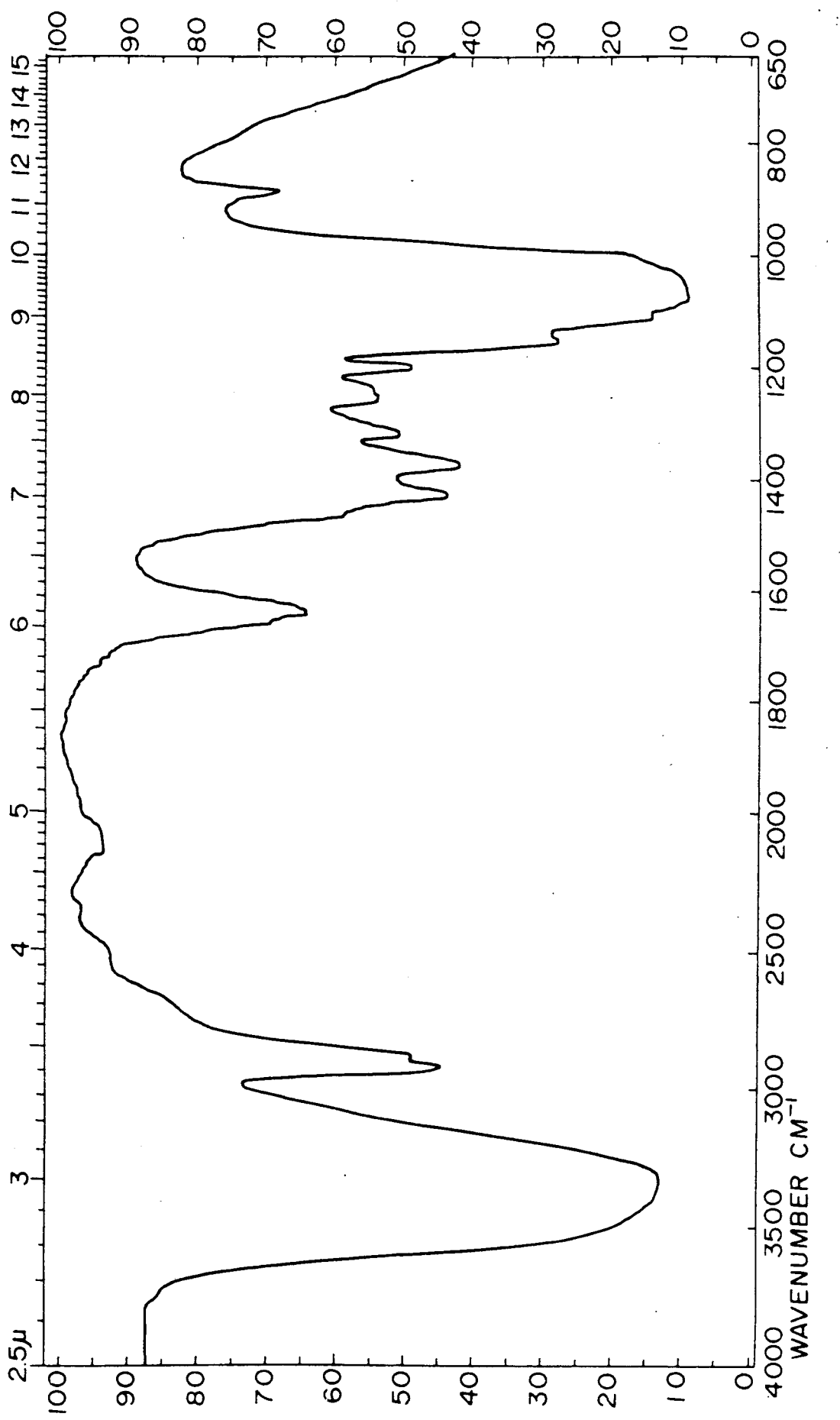
FIG. 1 is the infrared absorption spectrum of the polysaccharide.

Now, the present invention will be described in detail with reference to the preferred embodiments.

As the polysaccharide, schizophyllan produced by *Schizophyllum commune Fries*, scleroglucan produced by *Sclerotium glucanicum* and pendulan produced by *Porodisculus pendulus*. Since these homopolysaccharides can be extracellularly produced by culturing the respective strains, the separation and purification of the polysaccharides are easy.

The polysaccharide obtained by such culturing forms an extremely viscous and thixotropic aqueous solution, and its purification is usually difficult. To purify such polysaccharide to a high degree so that it may be used as a pharmaceutical intended by the present invention, it is advisable to lower the molecular weight by the depolymerization of the polysaccharide. Such depolymerization may preferably be conducted by irradiating ultrasonic waves to the aqueous polysaccharide solution or treating such polysaccharide solution with a high shear force. By such depolymerization, only the main chains composed of $\beta$-1,3- glucoside bonds of the polysaccharide, are selectivity cleaved, and the side chains composed of $\beta$-1,6-glucoside bonds remain uncleaved substantially.

Thus, the fundamental structure of the polysaccharide will be maintained unchanged even after the depolymerization.

To purify the polysaccharide to such an extent that it is capable of being used for the production of pharmaceuticals, the molecular weight of the polysaccharide is preferably lowered to a level of at most $10^6$ (n in the formula (1) being at most 1544), preferably at most $5 \times 10^5$ (n in the formula (1) being at most 772). If the molecular weight of the polysaccharide exceeds the above limit, it becomes difficult to conduct a purification operation such as filtration, ion exchange or active carbon treatment, since the aqueous solution will be highly viscous.

The polysaccharide used in the present invention is a polysaccharide containing $\beta$-1,3-linked backbone chain. Therefore, as opposed to polysaccharides having $\beta$-glucoside bonds, such as starch or dextran, it is scarcely decomposed by an enzyme in the living body and has a very low toxicity as its feature.

When the polysaccharide is sulfated, the sulfation may be conducted by any one of known methods. For example, it is possible to employ a method wherein sulfuric acid is used, a method wherein chlorosulfonic acid is used, or a method wherein sulfate trioxide is used. Among these methods, the chlorosulfonic acid method and the sulfate trioxide method employed in combination with a Lewis base, are particularly suitable for the prepration of the polysaccharide sulfate of the present invention, since the decomposition of the polysaccharide is thereby less than the method wherein sulfuric acid is used. As the Lewis base, pyridine, triethylamine, trimethylamine, dioxane or bis(2-chloroethyl) ether may be employed. Further, as a simplified method, it is possible to employ a sulfation method wherein a pyridine/sulfuric anhydride complex is reacted with the polysaccharide in pyridine or dimethylsulfoxide.

The prepared polysaccharide sulfate is usually kept in the form of a suitable salt in order to prevent it from hydrolysis. As the type of the salt, for example, an ammonium salt or an alkali metal salt such as a sodium salt is common. However, an alkaline earth metal salt, a metal salt such as an iron salt, or a salt with a quarternary amine, may also be employed.

The polysaccharide and its sulfate have the following infrared absorption spectra.

(a) The polysaccharide (FIG. 1)

Absorption attributable to stretching vibration of O-H at about 3,400 cm$^{-1}$, asymmetric stretching vibration of C—O—C at about 1,250 cm$^{-1}$, stretching vibration of C—O at about 1,050 cm$^{-1}$ and absorption characteristic of the $\beta$-glucoside at about 890 cm$^{-1}$.

Figure 2:
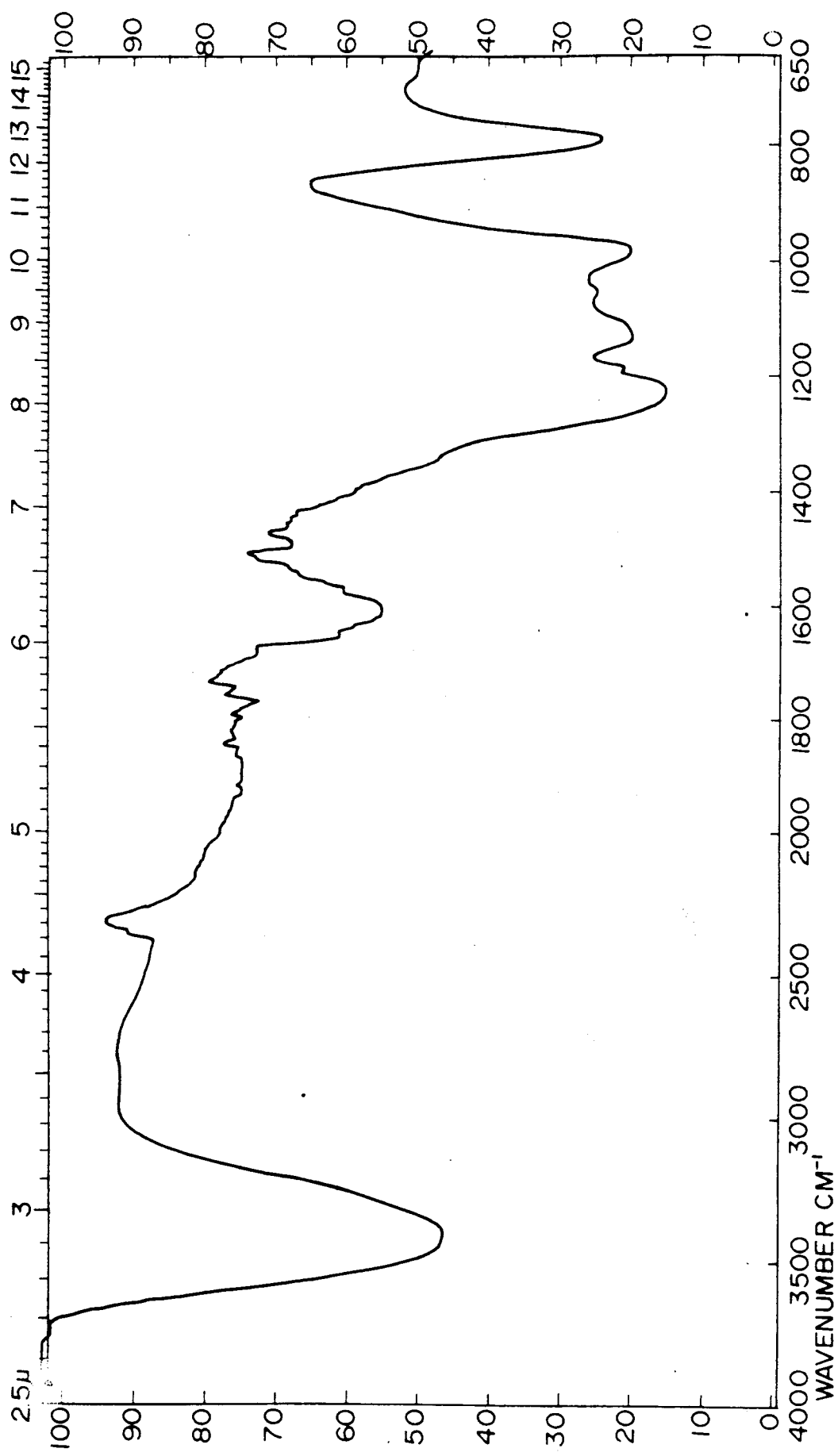
FIG. 2 is the infrared absorption spectrum of the sulfate of the polysaccharide.

(b) Sulfate of the polysaccharide (FIG. 2)

Absorption attributable to symmetric vibration of $SO_2$ about 1,240 cm$^{-1}$ and stretching vibration of C—O—S at about 810 cm$^{-1}$.

The present inventors have studied the correlation of the mitogenic or the anti-AIDS activities with the average molecular weight of the polysaccharide as the starting material used for the preparation of the polysaccharide sulfate or the sulfur content after the sulfation and the mitogenic activities or the anti-AIDS virus activities. As a result, it has been found that these physiological activities depend largely on the sulfur content after the sulfation rather than on the average molecular weight of the polysaccharide. Significant mitogenic activities are discernible at a sulfur content of the polysaccharide sulfate ranging from 2 to 17% by weight, and the anti-AIDS virus activities are obtainable at a sulfur content ranging from 3 to 17% by weight. If the sulfur content is less than 3% by weight, the anti-AIDS virus activities tend to be low. In the cytatoxicity tests of schizophyllan sulfate having a sulfur content of 17% by weight, no cytatoxicity was observed up to a concentration of 2,000 $\mu$g/ml. However, if the sulfur content is higher than this level, the product is believed to be unsuitable as a drug.

The anti-AIDS virus activities of the polysaccharide sulfate have low dependency on the molecular weight of the polysaccharide. Accordingly, the molecular weight of the polysaccharide to be used in the present invention may be at any level within a range suitable for adequate purification and is usually at most $10^6$ (n of the formula (1) being at most 1,544), preferably at most $5 \times 10^5$ (n of the formula (1) being at most 772).

The present inventors have also found that sulfates of other polysaccharides such as dextran, curdran and lentinan also have anti-AIDS virus activities at a sulfur content within substantially the same range as the above discovery with respect to schizophyllan. However, such a discovery is irrelevant to the present invention.

Now, the present invention will be described in further detail with reference to Examples. However, it should be understood that the present invention is by no means restricted by such specific Examples.

EXAMPLE 1

A sulfate of the polysaccharide was prepared by various methods, and its mitogenic activities and anti-AIDS virus activities were investigated.

(1) Preparation of schizophyllan sulfate

Method A 0.5 g or 1 g of schizophyllan was suspended in 100 ml of pyridine at 45° C. for 5 minutes. Then, a pyridine/sulfuric anhydride complex (from 2 to 6 g) was added thereto. The mixture was reacted under stirring at a temperature of from 60° to 70° C. for sulfation.

After the reaction, the precipitate was dissolved in a small amount of water, and free sulfuric acid was removed by centrifugation after converted to barium sulfate. The supernatant was concentrated under reduced pressure, and an excess amount of ethanol was added thereto to obtain a precipitate of a sulfate. The precipitate was dissolved in water for ion exchange treatment and then neutralized with NaOH. After concentration, ethanol was added to form a precipitate. The precipitate was collected by centrifugal separation, then dissolved in a small amount of water and freeze-dried to obtain schizophyllan sulfate (1) to (3) and (7) to (10).

Method B 1 g of schizophyllan was dissolved in 100 ml of dimethyl sulfoxide, and 3 g, 6 g or 9 g of a pyridine/sulfuric anhydride complex was added thereto. The mixture was reacted at room temperature for 5 minutes for sulfation.

After the reaction, the reaction solution was cooled with ice water. After removing the supernatant, the precipitate was dissolved by an addition of 50 ml of cold water thereto. The solution was neutralized by an addition of a saturated barium hydroxide aqueous solution. After removing the precipitate by centrifugation, the supernatant was subjected to dialysis. The non-dialyzate was concentrated under reduced pressure. An excess amount of acetone was added thereto, followed by centrifugation. The precipitate thereby obtained was dissolved in 50 ml of water for ion exchange treatment, then neutralized by an addition of 1N NaOH and freeze-dried to obtain schizophyllan sulfate (4) to (6).

Method C 25 ml of pyridine was introduced into a round bottom flask and cooled to $-10°$ C., and 5 ml of chlorosulfonic acid was gradually added under stirring at $-10°$ C. The mixture was reacted for from 15 to 20 minutes. The reaction product was dissolved at a temperature of from 60° to 70° C. Then, 1 g of schizophyllan was added thereto, and the mixture was vigorously stirred for one hour for sulfation.

After the reaction, the supernatant was removed, and the precipitate was dissolved in 100 ml of cold water and neutralized by an addition of a saturated sodium carbonate aqueous solution. An excess amount of acetone was added thereto to form a precipitate of the sulfate. The precipitate was recovered by centrifugation and dissolved by an addition of water and subjected to ion exchange treatment. Then, sodium carbonate was added to adjust the pH of the solution to from 9 to 10. An excess amount of acetone was added thereto to form a precipitate, and the precipitate was separated by centrifugation, then dissolved in a small amount of water and freeze-dried to obtain a polysaccharide sulfate (11) and (12).

Schizophyllan sulfates obtained by the forgoing methods are summarized in Table 1.

TABLE 1

| Polysaccharide used for reaction | | | | |
|---|---|---|---|---|
| Average Molecular weight | Weight (g) | Yield of its sulfate (g) | Sulfur content (wt %) | Sample No. |
| $45.5 \times 10^4$ | 1.0 | 0.25 | 1.96 | (1) |
| | 1.0 | 0.81 | 3.84 | (2) |
| | 1.0 | 1.0 | 13.7 | (3) |
| | 1.0 | 0.92 | 4.63 | (4) |
| | 1.0 | 0.92 | 7.07 | (5) |
| | 1.0 | 1.00 | 17.1 | (6) |
| $11.5 \times 10^4$ | 0.5 | 0.45 | 3.70 | (7) |
| | 0.5 | 0.74 | 4.20 | (8) |
| | 0.5 | 0.52 | 7.20 | (9) |
| | 0.5 | 0.45 | 10.7 | (10) |
| $3.10 \times 10^4$ | 1.0 | 0.87 | 9.70 | (11) |
| $1.15 \times 10^4$ | 1.0 | 0.56 | 10.0 | (12) |

(2) Study of the mitogenic activities of schizophyllan sulfates

A spleen of a mouse was aseptically taken out and dispersed in a culture medium to obtain a cell suspension containing $3 \times 10^6$ cells/ml. The cells were subdivided into wells of a 96 well-microplate so as to adjust the cell number in each well to $3 \times 10^5$. A culture medium and a sample were added to each well, followed by culturing for 3 days. On the third day, 0.5 μCi of $^3$H-thymidine was added to each well, and culturing was conducted for further 7 hours. Then, the cells were harvested and thoroughly washed, and the amount of $^3$H-thymidine taken into the cells was measured by a liquid scintillation counter.

Schizophyllan sulfates exhibited high mitogenic activities which were not observed in the case of schizophyllan.

TABLE 2

| | | | | |
|---|---|---|---|---|
| Mitogenic activities of schizophyllan sulfates | | | | |
| Sample No. | Average molecular weight of schizophyllan | Sulfur content in schizophyllan sulfate (wt %) | Count (CPM) | |
| | | | 100 μg/ml | 500 μg/ml |
| (1) | $45.5 \times 10^4$ | 1.96 | 5264 ± 536 | 11183 ± 1694 |
| (3) | $45.5 \times 10^4$ | 13.7 | 4262 ± 918 | 5325 ± 1479 |
| (5) | $45.5 \times 10^4$ | 7.07 | 3094 ± 833 | 6580 ± 532 |
| (7) | $11.5 \times 10^4$ | 3.7 | 23121 ± 2702 | 3881 ± 2914 |
| (9) | $11.5 \times 10^4$ | 7.2 | 23996 ± 5617 | 3374 ± 2703 |
| (11) | $3.1 \times 10^4$ | 9.7 | 13115 ± 5982 | 4294 ± 498 |
| (12) | $1.15 \times 10^4$ | 10.0 | 6483 ± 774 | 5108 ± 473 |
| Control | No compound added | | 2697 ± 1242 | |
| | Schizophyllan | | 1981 ± 184 | |
| | Con A added | | 52659 ± 6316 | |

(3) Study of the anti-AIDS virus activities of schizophyllan sulfates

Virus derived from Tall-1/HTLV-III were adsorbed on Molt-4/cl. No. 8 cells. Then, the cells were washed with a culture medium to remove virus not adsorbed on the cells. The cells thus obtained were subjected to the following test.

Into each well of a microplate having 24 wells, 1 ml of a cell suspension containing $3.5 \times 10^4$ cells/ml, 1 ml of a culture medium and a sample dissolved in PBS were added so that the final concentration of the sample would be 100 μg/ml. Culturing was conducted for 8 days, and cytopathic effects (CPE) by virus were observed. Further, on the 8th day, the supernatant of the culture medium was sampled and subjected to the measurement of reverse transcriptase activities. The cells were subjected to an indirect immunofluorescence assay to detect the virus antigen.

The results in the measurement of reverse transcriptase activities are shown in Table 3.

TABLE 3

Anti-AIDS virus activities of schizophyllan sulfates (Molt-4/cl. No. 8 cells)

| Sample No. | Average molecular weight of schizophyllan | Sulfur content in schizophyllan sulfate (wt %) | Sample concentration for reverse transcriptase activities (CPM) | |
|---|---|---|---|---|
| | | | 100 μg/ml | 500 μg/ml |
| (2) | $45.5 \times 10^4$ | 3.84 | 658 ± 33 | 843 |
| (3) | $45.5 \times 10^4$ | 13.7 | 593 ± 12 | 657 ± 14 |
| (6) | $45.5 \times 10^4$ | 17.1 | 663 ± 126 | 536 ± 82 |
| (7) | $11.5 \times 10^4$ | 3.70 | 329 ± 10 | 489 ± 234 |
| (8) | $11.5 \times 10^4$ | 4.20 | 324 ± 101 | 499 ± 1 |
| (9) | $11.5 \times 10^4$ | 7.20 | 248 ± 21 | 230 ± 27 |
| (10) | $11.5 \times 10^4$ | 10.7 | 393 ± 84 | 274 ± 86 |
| Control: | | | | |
| No compound added | Virus (−) | | 199 ± 32 | |
| | Virus (+) | | 27557 ± 528 | |
| | | | Sample concentration | |
| | | | 100 μg/ml | 500 μg/ml |
| Dextran sulfate (sulfur content: 13%) | | | 1947 ± 64 | 703 ± 56 |

As shown in Table 3, schizophyllan sulfates have strong anti-AIDS virus activities for distinctly suppressing proliferation of AIDS virus.

These schizophyllan sulfates completely suppressed the formation of giant cells, which were otherwise likely to be caused by cytopathic effects of AIDS virus. Further, no virus antigen was detected by the indirect immunofluorescence assay with the cells cultured together with these schizophyllan sulfates.

EXAMPLE 2

Further, anti-AIDS virus activities of schizophyllan sulfates were studied by using MT-4 cells.

Cells were prepared in the same manner as in Example 1(3), and into each well, 1 ml of a cell suspension containing $14 \times 10^4$ cells/ml, 1 ml of a culture medium and a sample solution were added, followed by culturing for 10 days.

The anti-AIDS virus activities of schizophyllan sulfates were studied by the observation of the cytopathic effects, by the measurement of reverse transcriptase activities and by the indirect immunofluorescence assay.

The results of the measurement of reverse transcriptase activities are shown in Table 4.

As shown in Table 4, schizophyllan sulfates exhibited strong anti-AIDS virus activities also in a cell line such as MT-4 cell which is highly sensitive to AIDS virus.

These samples (3), (10), (11) and (12) also suppressed formation of giant cells by cytophatic effects. No or little antigen was detected in the cells cultured together with these sulfates by the indirect immunofluorescence assay.

TABLE 4

Anti-AIDS virus activities of schizophyllan sulfates (MT-4 cells)

| Sample No. | Average molecular weight of schizophyllan | Sulfur content in schizophyllan sulfate (wt %) | Sample concentration for reverse transcriptase activities (CPM) | |
|---|---|---|---|---|
| | | | 100 μg/ml | 500 μg/ml |
| (3) | $45.5 \times 10^4$ | 13.7 | 17387 ± 1656 | 13257 ± 262 |
| (10) | $11.5 \times 10^4$ | 10.7 | 1863 ± 32 | 733 ± 201 |
| (11) | $3.1 \times 10^4$ | 9.7 | 559 ± 21 | 393 ± 13 |
| (12) | $1.15 \times 10^4$ | 10.0 | 4555 ± 741 | 1100 ± 172 |
| Control: No compound added | | | | |
| Virus (−) | | | 2481 ± 57 | |
| Virus (+) | | | 348764 ± 7996 | |
| Dextran sulfate (sulfur content: 13.0%) | | | 22317 ± 4502 | 18501 ± 2249 |

EXAMPLE 3

In the foregoing Examples, the anti-AIDS virus activities of schizophyllan sulfates were studied in a subcultured cell line. In this Example, a test was conducted for the effects of schizophyllan sulfates for suppressing proliferation of AIDS virus in a human peripheral lymphocytes system.

Lymphocytes were separated from peripheral blood of an AIDS patient by Ficoll-Paque Separation, washed three times with a serum-free culture medium and suspended in a culture medium containing 10% of FCS. Adsorbable cells were removed, and suspended cells were collected and suspended in a culture medium. Then, PHA and IL-2 were added thereto. Healthy human lymphocytes were prepared 3 days ahead by the above-mentioned method. Into each well of a microplate having 24 wells, $10^6$/1 ml of patient's lymphocytes, a culture medium, $10^6$/1 ml of healthy human lymphocytes and a schizophyllan sulfate solution were introduced, mixed and cultured. On the seventh day and eleventh day after initiation of the culturing, the supernatant was sampled and subjected to the measurement of reverse transcriptase activities. Into each well, a sampled supernatant and the same amount of a culture medium were introduced and culturing was continued.

The results are shown in Table 5.

TABLE 5

Anti-AIDS virus activities of schizophyllan sulfates in a human peripheral blood lymphocytes system

| Case | Concentration (μg/ml) | Reverse transcriptase activities (CPM) | | |
|---|---|---|---|---|
| | | 7th day | 11th day | 18th day |
| Sample (9) | 100 | 896 | 854 | 1055 |
| Case 1 (no addition) | | 268926 | 922938 | 515694 |
| Sample (9) | 100 | 168 ± 16 | 508 ± 37 | 825 ± 280 |
| Case 2 (no addition) | | 2872 ± 547 | 80436 ± 11982 | 67665 ± 1478 |
| Dextran sulfate (Sulfur content: 13.0%) | 100 | 1789 ± 53 | 42792 ± 14582 | 280741 ± 31039 |
| Sample (9) | 100 | 551 ± 7 | 640 ± 38 | 219 ± 20 |
| Case 3 (no addition) | | 501 ± 46 | 20669 ± 6966 | 339 ± 12 |

As is evident from the above Table, the anti-AIDS virus activities of schizophyllan sulfate were confirmed also with respect to human peripheral lymphocytes.

EXAMPLE 4

Schizophyllan is a polysaccharide having anti-tumor activities. Such activities may sometimes remain even after sulfation, and thus provides a feature which can not be found in other anti-AIDS virus agents.

$2 \times 10^6$ Sarcoma 180 cells were transplanted subcutaneously into the groins of mice. Twenty four hours later, 0.05 ml of a 0.5% PBS solution of schizophyllan sulfate was administered to a rear femoral muscle. Thirty days later, the mice were killed and dissected, and tumors were taken out and weighed. The tumor inhibition rates were culculated by the following equation.

$$\text{Tumor Inhibition ratio (\%)} = \frac{A - B}{A} \times 100$$

where A and B denote the average tumor weights (g) of the control group and the treated group.

Each group consisted of 6 mice. To the control group, PBS was administered in the same amount as in the tested group.

The results are shown in Table 6.

TABLE 6

Anti-tumor activities of schizophyllan sulfates

| Sample | Sulfur content (%) | Average weight (g) of tumor (wt ± S.E.) | Control rate (%) |
|---|---|---|---|
| Schizophyllan | — | 0.04 ± 0.016 | 99.0 |
| Schizophyllan sulfate (7) | 3.70 | 1.21 ± 0.613 | 70.3 |
| Schizophyllan sulfate (8) | 4.20 | 0.71 ± 0.251 | 82.6 |
| Schizophyllan sulfate (9) | 7.20 | 1.01 ± 0.371 | 75.2 |
| Schizophyllan sulfate (10) | 10.7 | 0.02 ± 0.014 | 99.5 |
| PBS | — | 4.07 ± 0.423 | — |

As is evident form the above results, strong anti-tumor activities are maintained in some of schizophyllan sulfates, which is regarded as a significant characteristic.

In the foregoing, usefulness of schizophyllan sulfates as anti-AIDS virus agents have been described with reference to some specific Examples.

Results of an acute toxicity test are shown in Table 7.

TABLE 7

Acute toxicity test of schizophyllan sulfates

| | Molecular weight of schizophyllan: $45.5 \times 10^4$; sulfur content: 10.7 wt % LD50 | Molecular weight of schizophyllan: $45.5 \times 10^4$; sulfur content: 18.1 wt % LD50 |
|---|---|---|
| Oral administration | At least 4,000 mg/kg | At least 4,000 mg/kg |
| Subcutaneous injection | At least 500 mg/kg | At least 100 mg/kg |
| Intramuscular injection | At least 500 mg/kg | At least 50 mg/kg |
| Intravenous injection | At least 200 mg/kg | At least 50 mg/kg |
| Intraperitoneal injection | At least 500 mg/kg | At least 50 mg/kg |

EXAMPLE 5

Ultrasonic waves were irradiated to aqueous solutions of scleroglucan and pendulan, which are polysaccharides composed of repeating units of the formula (1) like schizophyllan, to adjust the respective molecular weights to a level of 400,000. Then, they were sulfated in accordance with method A in Example 1 (polysaccharide: 0.5 g; pyridine/sulfuric anhydride complex: 5 g; reaction time: 5 hours) to obtain polysaccharide sulfates.

The anti-AIDS virus activities were studied with respect to the sulfates of scleroglucan and pendulan thus obtained, in accordance with the method as used in Example 1(3).

As the control, schizophyllan sulfate (sample (3)) in Example 1 and dextran sulfate were used. The results are shown in Table 8.

TABLE 8

Anti reverse transcriptase activities of sulfates of scleroglucan and pendulan

| Sample | Reverse transcriptase activities (CPM) Sample concentration | |
|---|---|---|
| | 100 μg/ml | 500 μg/ml |
| Scleroglucan sulfate | 669 ± 42 | 723 ± 26 |
| Pendulan sulfate | 646 ± 50 | 515 ± 83 |
| Schizophyllan sulfate | 739 ± 67 | 634 ± 37 |
| Dextran sulfate | 1781 ± 169 | 923 ± 32 |
| Control: | | |
| Virus (−) | 621 ± 47 | |
| Virus (+) | 51344 ± 2355 | |

As shown in Table 8, the sulfates of scleroglucan and pendulan exhibited stronger anti-AIDS virus suppressing activities than the dextran sulfate, like schizophyllan sulfate. Further, these sulfates completely suppressed formation of giant cells which were otherwise likely to be caused by cytophatic effects.

Further, no virus antigen was detected by the indirect immunofluorescence assay in the cells cultured together with these sulfates.

EXAMPLE 6

Schizophyllans having different molecular weights were sulfated in accordance with method A in Example 1 (polysaccharide: 0.5 g; pyridine/sulfuric anhydride complex: 5 g; reaction time: 5 hours). The anti-AIDS virus activities were studied with respect to the polysaccharide sulfates thus obtained, in accordance with the method as described in Example 1(3). As the control, dextran sulfate was used. The results are shown in Table 9.

TABLE 9

The dependency of the anti reverse transcriptase activities on the molecular weight of schizophyllan sulfates

| Molecular weight of schizophyllan | Sulfur content (wt %) | Reverse transcriptase activities (CPM) Sample concentration | |
|---|---|---|---|
| | | 100 μg/ml | 500 μg/ml |
| $1.1 \times 10^6$ | 9.3 | 705 ± 57 | 667 ± 42 |
| $7.6 \times 10^5$ | 11.7 | 632 ± 48 | 612 ± 43 |
| $4.55 \times 10^5$ | 13.7 | 693 ± 52 | 680 ± 50 |
| $3.2 \times 10^5$ | 7.9 | 445 ± 66 | 490 ± 58 |
| Dextran sulfate | 13.0 | 1738 ± 251 | 923 ± 87 |
| Control: | | | |
| Virus (−) | | 854 ± 53 | |
| Virus (+) | | 49291 ± 2035 | |

The anti-AIDS virus agent of the present invention comprises a polysaccharide sulfate which is prepared by sulfation of a homopolysaccharide consisting solely of glucose, resulting in its very potent anti-AIDS activity as well as the potent mitogenic activity in comparison with those of other sulfated polysaccharides. Further, the polysaccharide sulfate of the present invention has a sulfur content of from 3 to 17%, whereby it has a feature that it has a low toxicity while having strong anti-AIDS virus activities.

It has been proved that the anti-AIDS virus agent of the present invention has the anti-AIDS virus activities not only in a subcultured cell-line such as Molt-4/cl. No. 8 cells or MT-4 cells, but also in a human peripheral lymphocytes. This indicates that the polysaccharide sulfate of the present invention can be an excellent anti-AIDS virus agent.

Furthermore, the average molecular weight of the polysaccharide of the present invention is adjusted to be from 10,000 to 500,000, whereby various problems involved in the process for the production such as filtration and purification, can be solved, and a highly purified polysaccharide can be obtained. Accordingly, the anti-AIDS virus agent of the present invention can have a high quality as a drug.

We claim:

1. A sulfated polysaccharide having an average molecular weight of from 10,000 to at most 1,000,000, and a sulfur content of from 3 to 17% by weight, which polysaccharide is pendulan, or a salt thereof.

2. The sulfated polysaccharide according to claim 1, wherein the polysaccharide sulfate has a molecular weight of at most 500,000.

3. The sulfated polysaccharide according to claim 1, which is in the form of a salt.

4. The sulfated polysaccharide according to claim 3, wherein said salt is an ammonium salt, an alkali metal salt, an alkaline earth metal salt, an iron salt or a salt of a quaternary amine.

5. The sulfated polysaccharide according to claim 1, which is freeze-dried.

6. A pharmaceutical composition for treating an AIDS virus in mammals, which comprises, as an active ingredient, an amount of the sulfated polysaccharide of claim 1 effective for inhibiting said virus, and a pharmaceutically acceptable carrier.

* * * * *